United States Patent
Kraft et al.

[11] Patent Number: 5,874,315
[45] Date of Patent: Feb. 23, 1999

[54] METHOD FOR STAINING STOOL PARASITES

[75] Inventors: Jeffrey A. Kraft; Ching Sui A. Yi; David Huntington Willis, Jr., all of Cincinnati, Ohio

[73] Assignee: Meridian Diagnostics, Inc., Cincinnati, Ohio

[21] Appl. No.: 611,388

[22] Filed: Mar. 5, 1996

[51] Int. Cl.⁶ .................................................. G01N 1/30
[52] U.S. Cl. .................... 436/176; 435/40.5; 435/40.51; 436/174
[58] Field of Search ................... 436/174, 176, 436/18, 56; 435/40.5, 40.91

[56] References Cited

U.S. PATENT DOCUMENTS

| | | | |
|---|---|---|---|
| 4,129,093 | 12/1978 | Johnson | 118/301 |
| 4,199,613 | 4/1980 | Johnson . | |
| 4,666,699 | 5/1987 | Slifkin | 424/7.1 |
| 4,792,521 | 12/1988 | Shochat . | |
| 4,816,244 | 3/1989 | Starkweather . | |
| 4,847,208 | 7/1989 | Bogen | 436/174 |
| 4,906,451 | 3/1990 | Sims . | |
| 5,073,504 | 12/1991 | Bogen | 436/174 |
| 5,134,662 | 7/1992 | Bacus et al. . | |
| 5,225,325 | 7/1993 | Miller et al. | 435/6 |
| 5,322,771 | 6/1994 | Rybski et al. . | |
| 5,418,138 | 5/1995 | Miller et al. . | |
| 5,508,175 | 4/1996 | Slifkin | 435/40.5 |

OTHER PUBLICATIONS

Chemical Abstracts, CA 123:334055. Ono et al., "Improved Method of Elastic Fiber Staining . . . ", Igaku Kensa (1995), 414(9). pp. 1410–1415.

Chemical Abstracts, CA 99:154652. Crowder, "The Trichrome Stain: A Modification," J. Histotechnol. (1983), 6(3), pp. 133–134.

Chemical Abstracts, CA 89:144784. Furlan et al. "Histochemical Detection . . .," Boll. Soc. Ital. Biol. Sper. (1978), 54(3), pp. 258–263.

Chemical Abstracts, CA 83:175085. Hogg et al. "Evaluation of Solochrome Cyanine RS . . . " Med. Lab. Technol. (1975), 32(4), pp. 301–306.

*Primary Examiner*—Jan Ludlow
*Attorney, Agent, or Firm*—Thompson Hine & Flory LLP

[57] ABSTRACT

A method for staining fecal specimens to diagnose stool parasites preserved with a non-mercury fixative wherein the preserved specimen is stained with a composition of iron hematoxylin stain and trichrome stain.

5 Claims, 5 Drawing Sheets

*Giardia lamblia* Trophozoites
Stained with EcoStain and Trichrome

METHOD FOR STAINING STOOL PARASITES

BACKGROUND OF THE INVENTION

The present invention relates to a method for staining a fecal specimen preserved using a non-mercury based fixative. More particularly, the invention provides a method which utilizes a stain which is a combination of iron hematoxylin stain and trichrome stain for staining fecal specimens preserved in non-mercury based fixatives.

The most widely used method for detecting and identifying gastrointestinal parasites is the microscopic examination of fecal specimens in the laboratory. Ordinarily, a part of this microscopic examination involves staining the specimen in order to enable the clinician to differentiate between organisms which, unstained, are very difficult to distinguish with accuracy.

Because parasites are fragile and can change or deteriorate in the time which elapses before they are examined, specimens must be examined immediately or must be preserved with a suitable fixative. Timely collection and transportation of fresh stool specimens to the laboratory cannot always be assured and workload conditions and priorities in clinical laboratories frequently do not permit immediate examination of fresh specimens. Procedures such as incubation, refrigeration or freezing do not guarantee the recovery of all diagnostic stages of all parasites. Therefore, to prevent the degradation and loss of stool parasites from a specimen, fixatives are used to preserve the specimen.

Conventionally, mercury based fixatives have been used to preserve stool specimens for staining and microscopic parasitological examination. Stool parasites that have been preserved in mercury based fixatives provide good definition of the parasite upon staining. However, mercury based fixatives have a number of disadvantages associated with them that limit their use and have prompted laboratories to adopt non-mercury fixatives. In particular, the use and disposal of mercury is regulated under federal and state environmental laws.

Non-mercury based fixatives for parasitological examination have been developed in recent years in response to the health and environmental concerns associated with mercury based preservatives. These fixatives typically include non-mercury metals zinc or copper together with polymers such as polyvinyl alcohol. Specimens prepared in non-mercury based fixatives do not stain with the intensity, contrast and resolution compared to stained stool specimens which have been preserved in mercury based fixatives. This makes it more difficult and tedious to detect and identify the parasites. Accordingly, there is a need for a methodology for staining non-mercury fixed specimens which provides improved contrast and intensity.

Trichrome stain and iron hematoxylin stain are two stains frequently used in diagnostic parasitology. The trichrome stain works excellently with mercury fixed fecal specimens but does not work nearly as well when used with non-mercury fixatives. As a result, attempts have been made to find better stains for specimens fixed with non-mercury fixatives.

One prior art attempt to develop an improved stain is described in U.S. Pat. No. 4,666,699 to Slifkin, which teaches a stain-fixative composition for enteric parasites for use with mercury-free and formalin-free fixatives. The composition contains Ponceau S Stain, Chlorazol Fast Pink BK Stain, Trypan Blue Stain, dimethyl sulfoxide and a non-mercury, non-formalin based fixative.

There continues to be a need for a method for staining stool parasite specimens which have been preserved in non-mercury based fixatives that produces significantly better overall staining quality, intensity and contrast.

The present invention is based on the discovery that iron hematoxylin stain and trichrome stain can be mixed and used effectively to stain fecal specimens preserved with non-mercury fixatives. Surprisingly, these two stains are not incompatible, they do not interact, they are not redundant, they intensify each other and in combination they stain fecal specimens with an intensity and resolution that is significantly better than can be achieved using either stain alone or in sequence. Whereas trichrome stain and hematoxylin stain when used alone with non-mercury fixatives give a low contrast microscope image which is difficult and time consuming to view and evaluate, when combined they yield an image which is intense and much easier to read and evaluate. The method of the present invention facilitates more accurate and precise detection of stool parasites by producing significantly better overall staining quality, intensity and contrast than previous methods for staining stool parasites preserved in non-mercury based fixatives.

SUMMARY OF THE INVENTION

Figure 1:
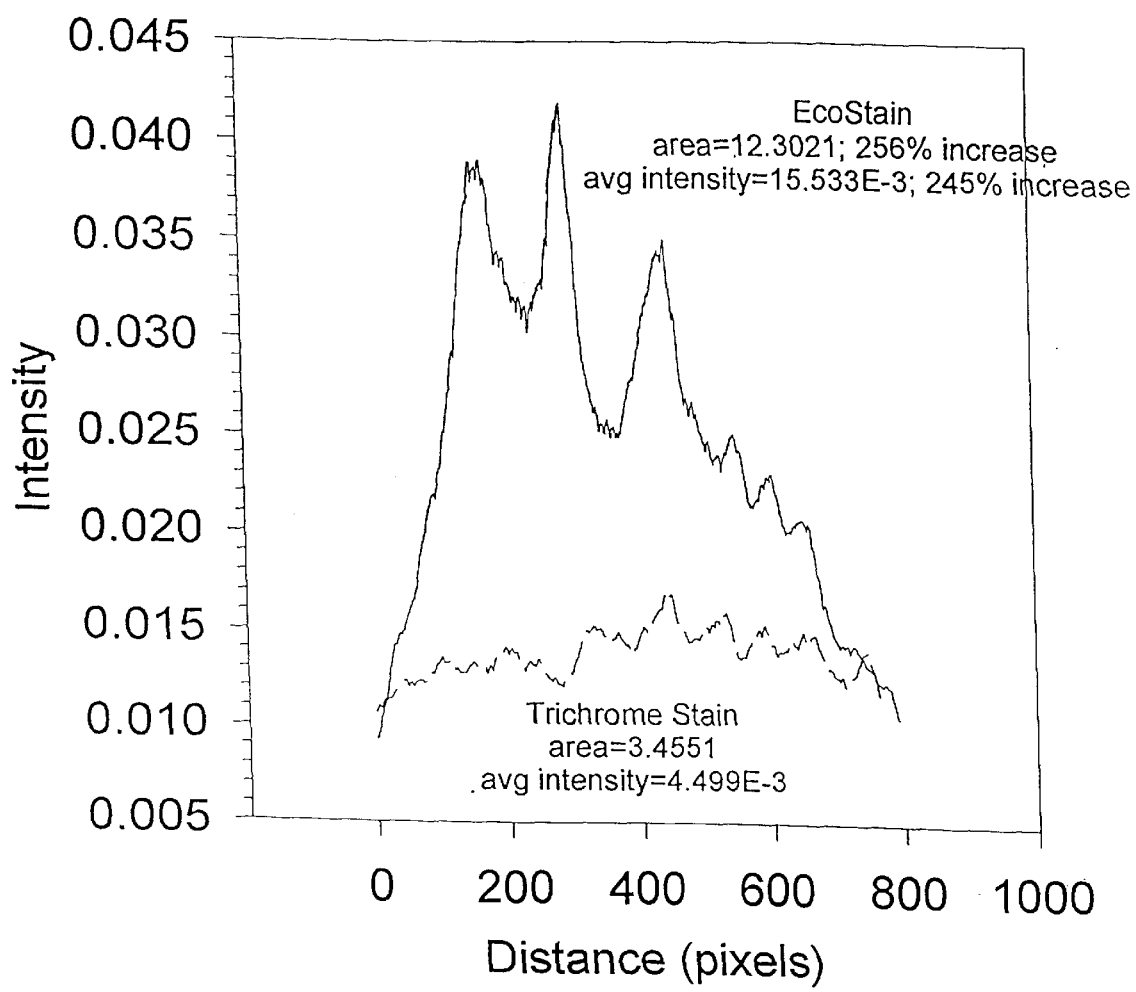
FIG. 1 is a graph comparing intensity vs distance or position for a grayscale bitmap of an image of G. lamblia trophozoites stained with Trichrome stain (curve A) and the stain of the present invention (Curve B).

The present invention is a method for staining fecal specimens which have been preserved in non-mercury based fixatives which comprises preserving the specimen using a non-mercury fixative and staining the specimen using a composition comprising a combination of iron hematoxylin stain and trichrome stain.

Accordingly, it is an object of the present invention to provide an improved method for staining fecal specimens which have been preserved in non-mercury based fixatives.

Other objects and advantages of the present invention will be apparent from the following description and the appended claims.

DETAILED DESCRIPTION

The method of the present invention is useful in the parasitological examination of stool specimens for parasites such as protozoa.

Examples of stool parasites that can be detected by using the method of the present invention include, but are not limited to *Entamoeba histolytica, Entamoeba hartmanni, Entamoeba coli, Endolimax nana, Dientamoeba fragilis, Giardia lamblia, Chilomastix mensnili, Iodamoeba butschlii, Balantidium coli, Blastocystis hominis,* etc. Protozoa can be detected as the cyst and/or trophozoite.

A stool specimen suspected of containing a stool parasite is collected and preserved in a manner known in the art. Examples of non-mercury based fixatives include, but are not limited to zinc or copper based fixatives and, more particularly, zinc-polyvinyl alcohol and copper-polyvinyl alcohol. One commercially available fixative with which the invention is particularly useful is ECOFIX and is commercially available from Meridian Diagnostics, Inc.

The fecal specimen may be placed directly into a receptacle containing the fixative at the time the specimen is collected. The receptacle is then sealed, shaken and dispatched to the laboratory in a conventional manner. The sealed receptacle typically contains both the fecal specimen and about 2 to 4 parts by volume of fixative based on one part fecal specimen.

In the method of the present invention, the preserved fecal specimen is smeared on a slide and the prepared slide is dried completely and then immersed into a solution containing iron hematoxylin stain and trichrome stain. In a preferred embodiment of the invention, the composition is prepared by mixing Weigert's Iron Hematoxylin Stain and Wheatley's Modified Trichrome Stain. Due to the inherent instability of iron hematoxylin stain, it is sold as a two part system which is mixed prior to use. Weigert iron hematoxylin stain is prepared by mixing 1% (w/v) hematoxylin in 95% alcohol with 1.2% ferric chloride and 1% hydrochloric acid in distilled water. Those skilled in the art will appreciate that other ferric salts, such as ferric ammonium sulfate and others, may be used in the iron hematoxylin stain. The trichrome stain is a mixture of Chromotrope 2R (C.I. 16570), Fast Green FCF (C.I. 42053) and Light Green S.F. The Wheatley's trichrome strain is an aqueous solution of 0.586% Chromotrope 2R, 0.147% Fast Green FCF and 0.147% Light Green SF, 0.684% phosphotungstic acid and 1.025% acetic acid. Both stains and their methods of production are well known in the art. It is desirable that the concentration ratio of iron hematoxylin stain solution to trichrome stain solution is in the range from about 40:60 to about 60:40 and preferably about 1:1 by volume.

It is desirable that the slide is immersed into the combined stains for a time sufficient to adequately stain the fecal specimen. About 8 minutes is normally sufficient. Typically, after the staining process, the slide is destained, dehydrated and cleared using well known laboratory procedures which involve sequentially immersing the slide into progressively more hydrophobic organic media and lastly, into a clearing agent. In one such procedure, after staining, the slide is initially immersed into a 90% acid-alcohol solution containing 0.5% acetic acid in ethyl alcohol to destain the slide. Following the acid-alcohol destaining step, the slide is placed into a 95–100% ethyl alcohol solution for a few seconds and then into a second 95–100% ethyl alcohol solution for about 5 minutes. Thereafter, it is desirable to immerse the slide into a carbol xylene solution containing 25% phenol and 75% xylene for about 10 minutes. To complete the dehydration/clearing process, the slide is immersed in a clearing agent such as xylene or a xylene substitute such as HEMO-DE for about 10 minutes.

In order for a clinical parasitology laboratory to examine the prepared slide, it is desirable that the slide is mounted and examined in a conventional manner. Preferably, the slide is mounted in Permount and examined by light microscopy.

The invention is illustrated in more detail by the following nonlimiting examples.

EXAMPLE 1

*Giardia lamblia* trophozoites were stained by placing a slide carrying a dried smear of a fecal specimen containing the parasite which had been fixed using the nonmercury fixative, ECOFIX, into a solution prepared by mixing (A) one part by volume of an iron hematoxylin stain solution prepared by mixing 1% (w/v) hematoxylin in 95% alcohol with 1.2% ferric chloride and 1% hydrochloric acid in distilled water with (B) one part by volume of a Wheatley's trichrome strain solution of 0.586% Chromotrope 2R, 0.147% Fast Green FCF and 0.147% Light Green SF, 0.684% phosphotungstic acid and 1.025% acetic acid in water. For comparison a second slide carrying a dried smear of the same specimen was stained using the Wheatley's stain (part B) alone. After staining, each slide was destained, dehydrated and cleared using the procedure described above. Photographs were then taken of each specimen using an Olympus microscope at 1000× magnification and Fuji Photo Film Company ASA 100 color print film. The photographs were developed and scanned with a 1200 dpi Mustek MFS-photographs 6000 CX scanner operating at 80% brightness and 64% contrast. The scans were converted to a grayscale bitmap and sampled at 25 pixel line widths to prepare graphs of intensity versus pixel or position for each slide. The graphs are shown in FIG. 1 where Curve A corresponds to the specimen stained with the trichrome stain and Curve B corresponds to the specimen stained in accordance with the invention. The graphs show that the stain of the invention provides about a 245% increase in intensity over the trichrome stain alone.

EXAMPLE 2

Figure 2:
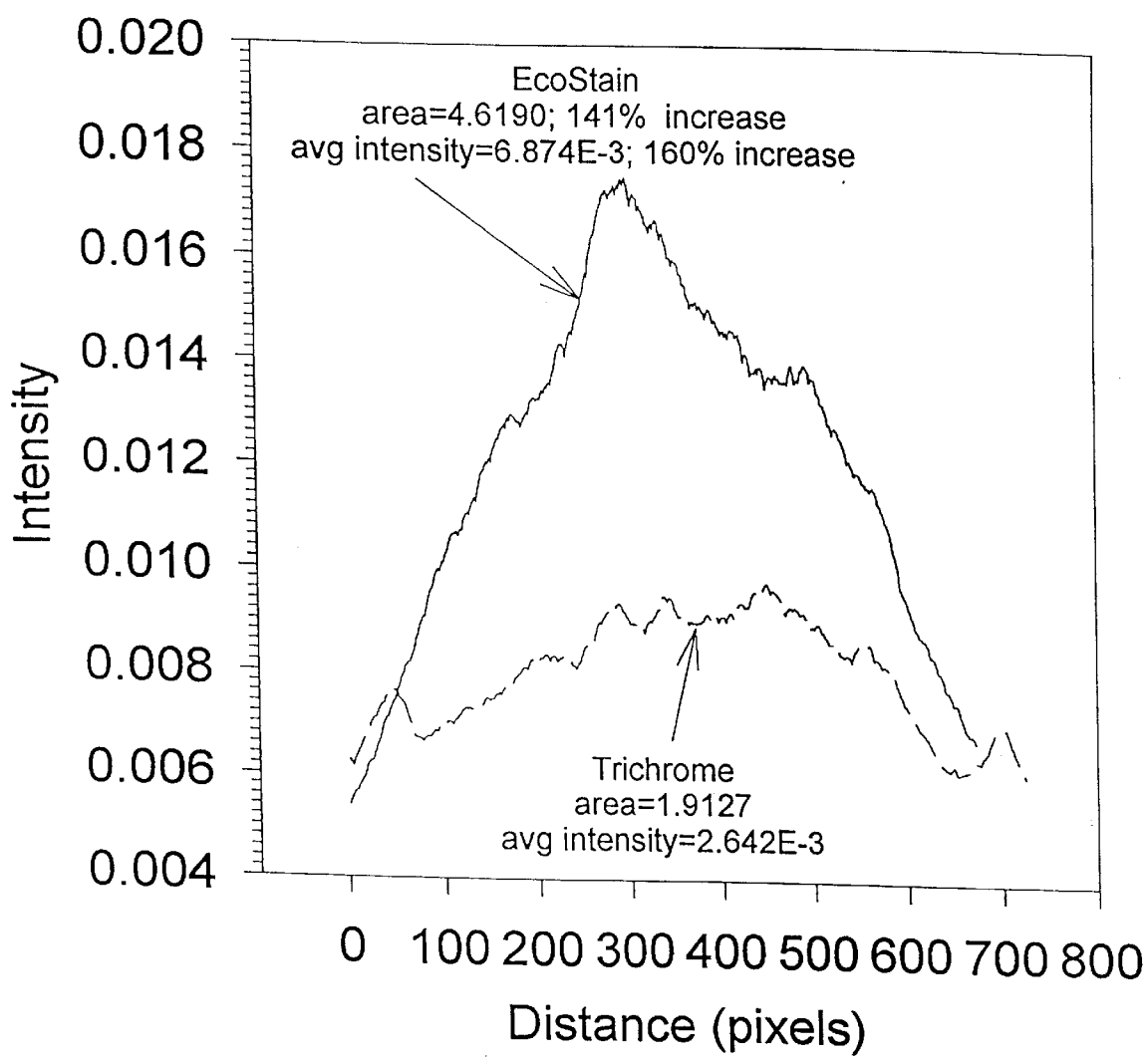
FIG. 2 is a graph comparing intensity vs distance or position for a grayscale bitmap of an image of G. lamblia cysts stained with Trichrome stain (curve A) and the stain of the present invention (Curve B).

Two slides carrying a dried smear of a fecal specimen containing *Giardia lamblia* cysts which had been fixed using ECOFIX were stained as in Example 1 and graphs were prepared as in Example 1 except that the slides were photographed using Kodak ASA 25 color print film. The graph is shown in FIG. 2 where Curve A corresponds to the specimen stained with the trichrome stain and Curve B corresponds to the specimen stained in accordance with the present invention. The curves in FIG. 2 show that the invention provides approximately a 160% improvement in intensity as compared to specimens stained using trichrome stain alone.

EXAMPLE 3

Figure 3:
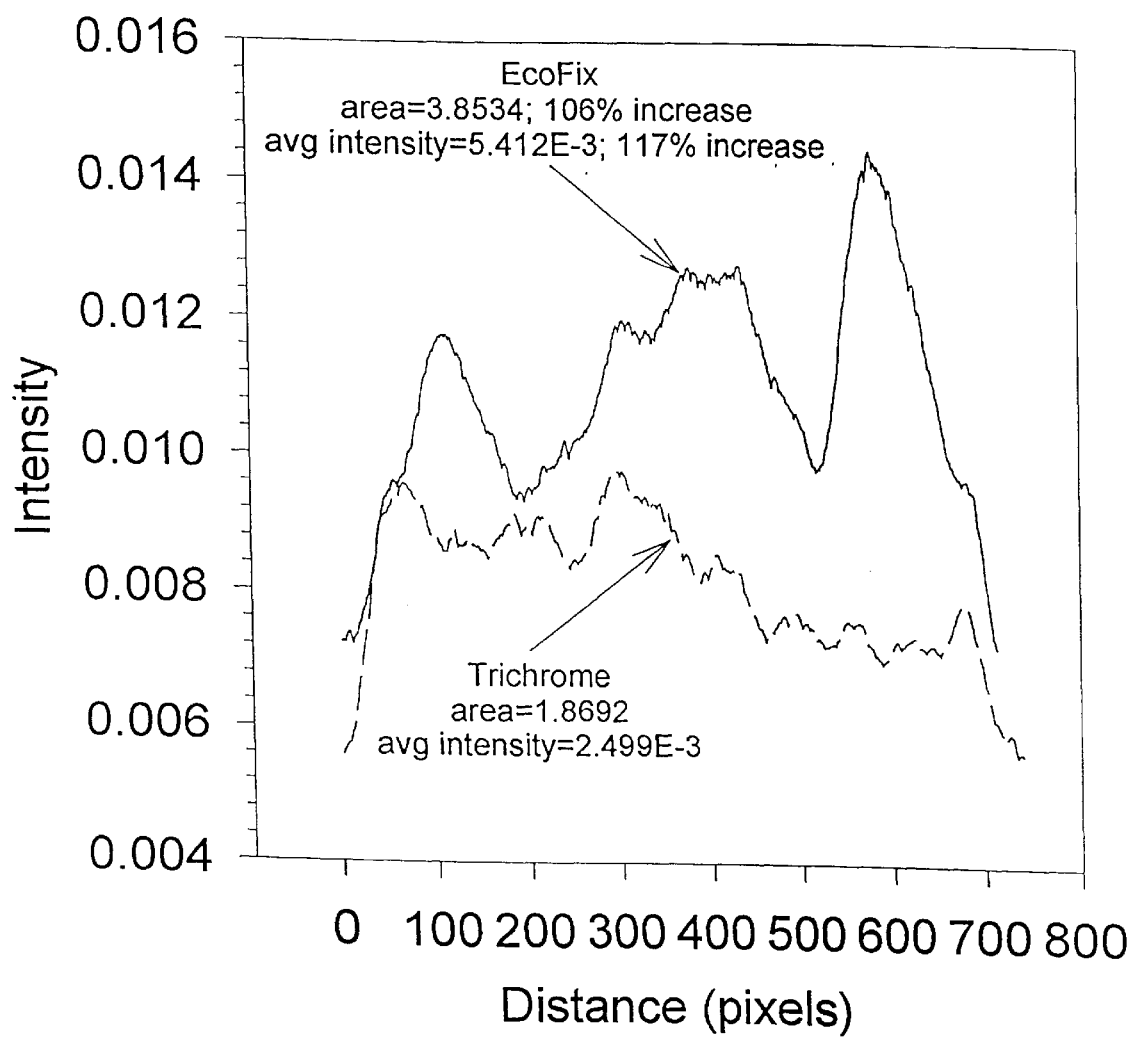
FIG. 3 is a graph comparing intensity vs distance or position for a grayscale bitmap of an image of E. hartmanni stained with Trichrome stain (curve A) and the stain of the present invention (Curve B).

Two slides carrying a dried smear of a fecal specimen containing *Entamoeba hartmanni* trophozoites which had been fixed using ECOFIX were stained as in Example 1 and graphs were prepared as in Example 1 except that the slides were photographed using Kodak ASA 25 color print film. The graph is shown in FIG. 3 where Curve A corresponds to the specimen stained with the trichrome stain and Curve B corresponds to the specimen stained in accordance with the present invention. The curves in FIG. 3 show that the invention provides approximately a 117% improvement in intensity as compared to specimens stained using trichrome stain alone.

EXAMPLE 4

Figure 4:
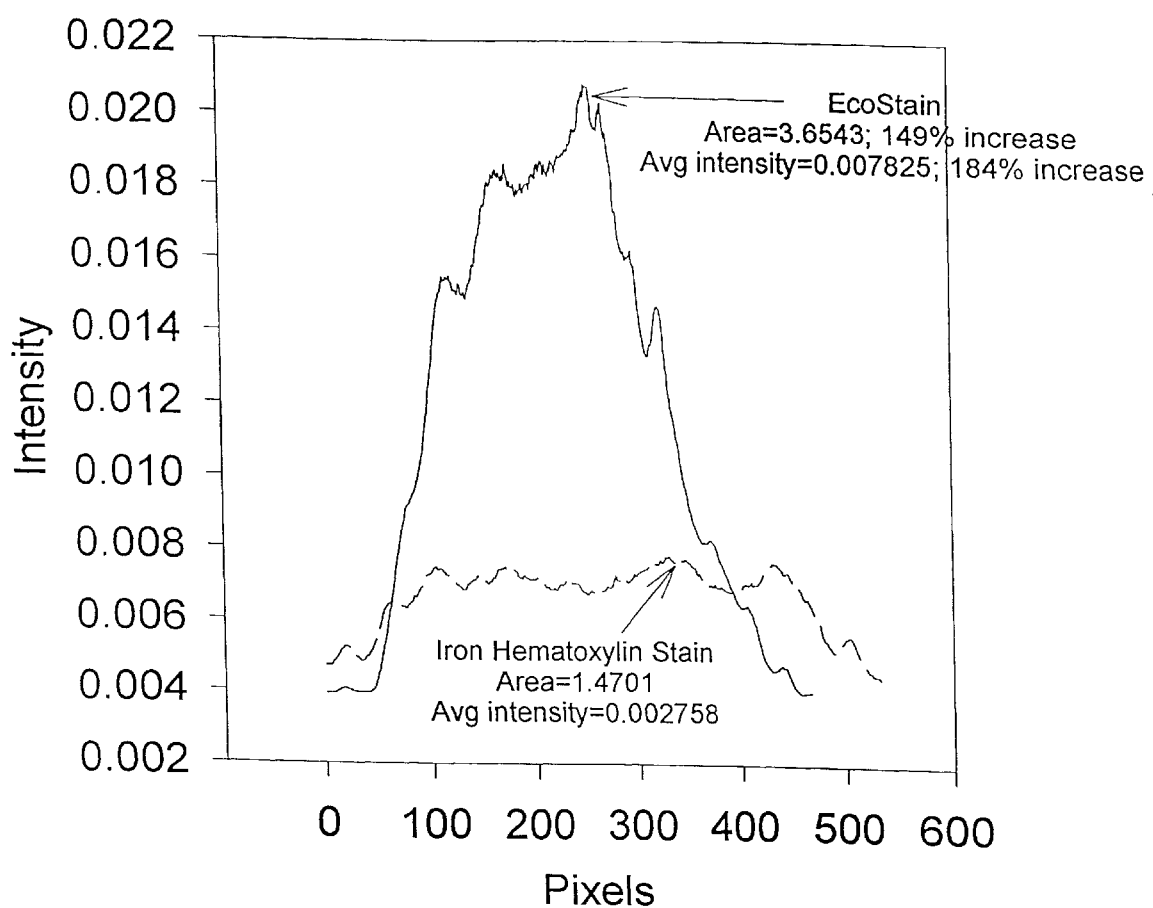
FIG. 4 is a graph comparing intensity vs distance or position for a grayscale bitmap of an image of G. lamblia cysts stained with Iron Hematoxylin stain (curve A) and the stain of the present invention (Curve B).

*Giardia lamblia* cysts were stained by placing a slide carrying a dried smear of a fecal specimen containing the parasite which had been fixed using the nonmercury fixative, ECOFIX, into a solution prepared by mixing (A) one part by volume of an iron hematoxylin stain solution prepared by mixing 1% (w/v) hematoxylin in 95% alcohol with 1.2% ferric chloride and 1% hydrochloric acid in distilled water with (B) one part by volume of a Wheatley's trichrome strain solution of 0.586% Chromotrope 2R, 0.147% Fast Green FCF and 0.147% Light Green SF, 0.684% phosphotungstic acid and 1.025% acetic acid in water. For comparison a second slide carrying a dried smear of the same specimen was stained using the iron hematoxylin stain (part A) alone. After staining, each slide was destained, dehydrated and cleared using the procedure described above. Photographs were then taken of each specimen using an Olympus microscope at 1000× magnification and Kodak ASA 25 color print film. The photographs were developed and scanned with an Epson-1000C scanner at 600 dpi. The scans were converted to a grayscale bitmap without brightness and contrast adjusted and sampled one line/organism across width at 25 pixel line width to prepare graphs of intensity versus pixel or position for each slide. The graphs are shown in FIG. 4 where Curve A corresponds to the specimen stained with the iron hematoxylin stain and Curve B corresponds to the specimen stained in accordance with the invention. The graphs show that the stain of the invention provides about a 184% increase in intensity over the iron hematoxylin stain alone.

EXAMPLE 5

Figure 5:
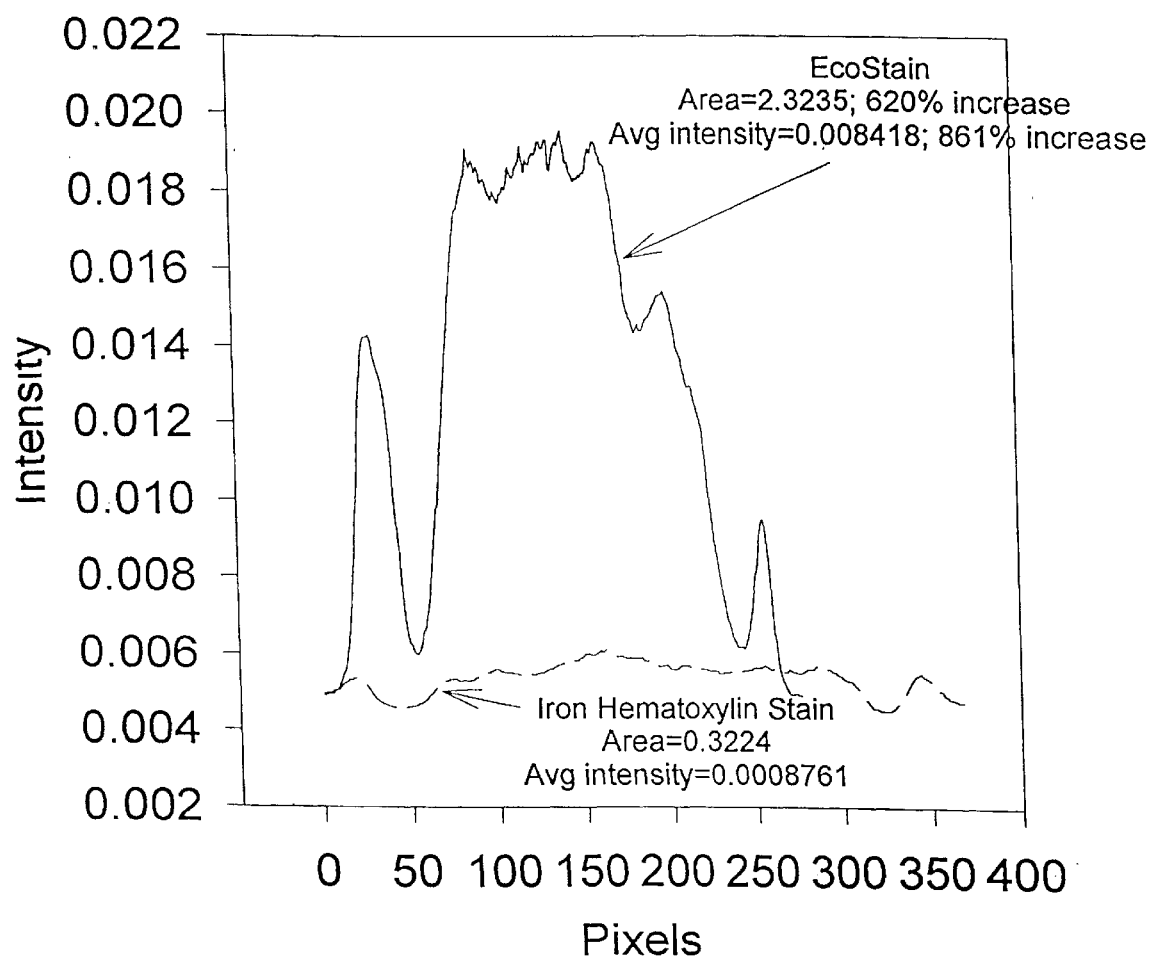
FIG. 5 is a graph comparing intensity vs distance or position for a grayscale bitmap of an image of Blastocystis hominis stained with Iron Hematoxylin stain (curve A) and the stain of the present invention (Curve B).

Two slides carrying a dried smear of a fecal specimen containing *Blastocystis hominis* which had been fixed using ECOFIX were stained, photographed and scanned as in Example 4. The graph is shown in FIG. 5 where Curve A corresponds to the specimen stained with the iron hematoxylin stain and Curve B corresponds to the specimen stained in accordance with the present invention. The curves in FIG. 5 show that the invention provides approximately a 861% improvement in intensity as compared to specimens stained using iron hematoxylin stain alone.

Having described the invention in detail and by reference to the preferred embodiments it will be apparent to those skilled in the art that modifications and variations are possible without departing from the scope of the invention as defined in the following appended claims.

We claim:

1. A method for staining a fecal specimen which comprises:
    preserving said specimen using a non-mercury fixative and staining said specimen using a composition comprising iron hematoxylin stain and trichrome stain.
2. The method of claim 1 wherein the non-mercury fixative is a copper or zinc fixative.
3. The method of claim 2 wherein the non-mercury fixative is zinc-polyvinyl alcohol or copper-polyvinyl alcohol.
4. The method of claim 2 wherein the iron hematoxylin stain and trichrome stain are in a concentration ratio in the range from about 60:40 to about 40:60.
5. The method of claim 4 wherein the concentration ratio is about 1:1.

* * * * *